US009683952B2

(12) United States Patent
Shields et al.

(10) Patent No.: US 9,683,952 B2
(45) Date of Patent: Jun. 20, 2017

(54) TEST STAND FOR XRF INSTRUMENT ENABLING MULTI-WAY OPERATION

(71) Applicants: Ted Michael Shields, Arlington, MA (US); Michael Drummy, Reading, MA (US); David Joyce, Chelmsford, MA (US); Matthew Thomas Susa, Ashburnham, MA (US)

(72) Inventors: Ted Michael Shields, Arlington, MA (US); Michael Drummy, Reading, MA (US); David Joyce, Chelmsford, MA (US); Matthew Thomas Susa, Ashburnham, MA (US)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 123 days.

(21) Appl. No.: 14/563,596

(22) Filed: Dec. 8, 2014

(65) Prior Publication Data

US 2015/0212018 A1 Jul. 30, 2015

Related U.S. Application Data

(60) Provisional application No. 61/931,023, filed on Jan. 24, 2014.

(51) Int. Cl.
*G01N 23/223* (2006.01)
(52) U.S. Cl.
CPC ..... *G01N 23/223* (2013.01); *G01N 2223/303* (2013.01)

(58) Field of Classification Search
CPC .......... G01N 23/223; G01N 2223/076; G01N 2223/301
See application file for complete search history.

(56) References Cited

U.S. PATENT DOCUMENTS

2010/0278312 A1* 11/2010 Ortiz .................... G01N 23/223
378/195
2011/0079734 A1 4/2011 Grodzins et al.

FOREIGN PATENT DOCUMENTS

CN 100379382 C 4/2008
CN 201177606 Y 1/2009

* cited by examiner

*Primary Examiner* — Hoon Song
(74) *Attorney, Agent, or Firm* — C. Tricia Liu

(57) ABSTRACT

Disclosed is a test stand that supports and stabilizes a handheld XRF analyzer, and holds a body of sample to be tested. The test stand allows both horizontal and vertical analysis positions of the analyzer. The preferred embodiment of the test stand comprises a shielded X-ray chamber in which samples are tested and which affixes to the XRF analyzer's window via a spring loaded handle, a stabilizing base to which the analyzer's handle is situated, and a stanchion for horizontal mounting of the XRF analyzer. In the horizontal orientation, the chamber contains an adjustable platform and soil sample retainer to facilitate the positioning of the sample to be tested. The stanchion can be stored under the base.

15 Claims, 7 Drawing Sheets

TEST STAND FOR XRF INSTRUMENT ENABLING MULTI-WAY OPERATION

RELATED APPLICATIONS

This application claims benefit of and priority to U.S. Provisional Application entitled "A TEST STAND FOR XRF INSTRUMENT ENABLING MULTI-WAY OPERATION" with application No. 61/931,023 filed Jan. 24, 2014 under 35 U.S.C. §119, 120, 363, 365, or 37 C.F.R. §1.55 or §1.78 incorporated herein by this reference.

BACKGROUND OF THE INVENTION

Test stands or work stations are used to hold small samples in an X-ray shielded chamber to allow the user to safely and conveniently analyze small samples. In a traditional test stand or work station for X-ray fluorescent (XRF) handheld analyzers, the analyzer is attached or suspended underneath an analysis deck. The deck is held up by a tripod or similar leg structure. This arrangement makes it very inconvenient to see the screen of the analyzer, and very difficult to run the analyzer using the touch screen.

Manufacturers have circumvented this problem by controlling the analyzer via connection to a Personal Computer (PC). However the PC solution requires the additional expense of acquiring or carrying a PC, and the inconvenience of requiring a PC connection.

Yet another challenge in positioning the XRF analyzer is that XRF samples needs certain force, such as gravity to be used to push the sample intimately against the analyzer's measurement window. Therefore certain test stand configurations might provide easier access to viewing the screen, but fall short in positioning the sample properly.

Some test stand alternatives place the sample in an X-ray shielded container, and then place the analyzer on top of the sample. This option runs the risk of the analyzer measurement window being punctured by the sample (if the sample is jagged), causing expensive repairs.

Additionally the tripod approach of traditional test stands requires some clearance below the analyzer to allow a user to install the analyzer in the test stand. This results in extra height, greater instability and tendency of tipping the analyzer and stand.

Thus, there is a need for a test stand that allows the user to safely and conveniently control and view an XRF analyzer from the screen, with XRF sample properly placed and with no PC attachment.

SUMMARY OF THE INVENTION

Disclosed is a supporting test stand that can be configured horizontally and vertically for supporting a handheld XRF analyzer instrument. A sample test chamber, stanchion, and base interlock with the snout (window) and the handle of the XRF analyzer instrument to provide robust stability. The user can choose the preferred configuration of the test stand for a given application.

In the horizontal configuration, the test screen of the XRF analyzer is readily visible and accessible by means of a stanchion. The sample chamber has an adjustable height platform floor, and a wedge feature as a soil sample retainer to help position the sample in front of the analyzer's measurement window.

In the vertical configuration, the disclosed test stand has the benefit of using gravity to maintain the sample's contact with the analyzer's measurement window, and is vertically configurable to offer the entire sample positioning advantages provided by traditional test stands. The stanchion can be stored under the base of the test stand.

DETAILED DESCRIPTION OF THE INVENTION

Table 1 is purposed for assisting the reading of this disclosure, and should not be construed as a limitation of its scope.

TABLE 1

| Components of the present disclosure | |
| --- | --- |
| Numeral in drawings | Associated component |
| 2 | Analyzer |
| 10 | Test stand |
| 12 | Base |
| 14 | Stanchion |
| 16 | Test chamber |
| 18 | Stability collar |
| 20 | Release handle |
| 20' | Locking pin receptacles |
| 21 | Stability wing |
| 22 | Soil sample retainer |
| 23 | Handle cradle |
| 24 | Interface plate |
| 24' | Interface plate tongue |
| 25 | Cavity |
| 26 | Stanchion receiver |
| 26' | Stanchion leads |
| 27 | Snout receiver |
| 27' | Snout |
| 28 | Magnet |
| 30 | Test platform |
| 32 | Test platform adjustment knob |
| 70 | Test chamber door |

It should be understood that various changes may be made and equivalents may be substituted for elements thereof without departing from the spirit and scope of the invention. The embodiment described herein and the claims described hereof are not to be read restrictively, unless there is clear and convincing evidence manifesting a certain exclusion, restriction, or disclaimer.

Figure 1A:
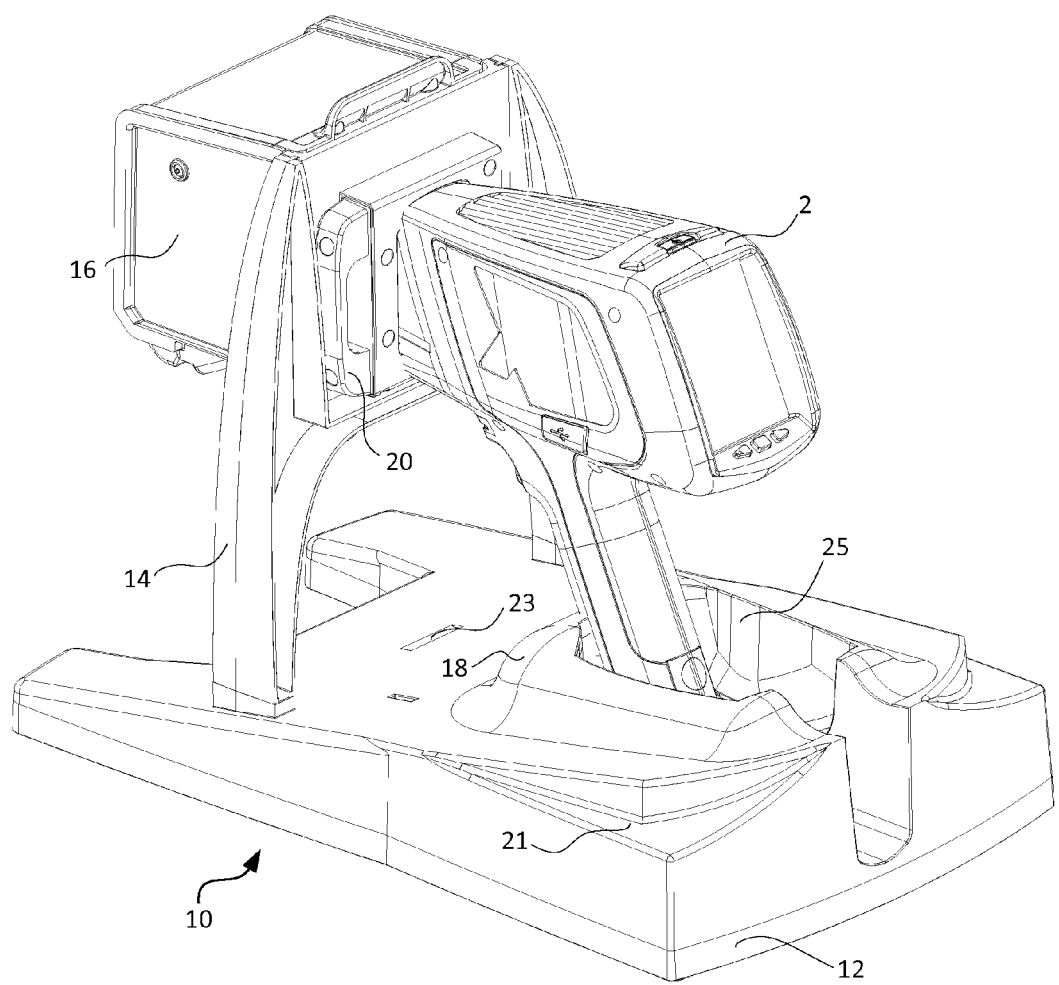
FIG. 1A is a perspective view of the test stand and the XRF analyzer in its horizontal position according to the present disclosure.
Figure 1B:
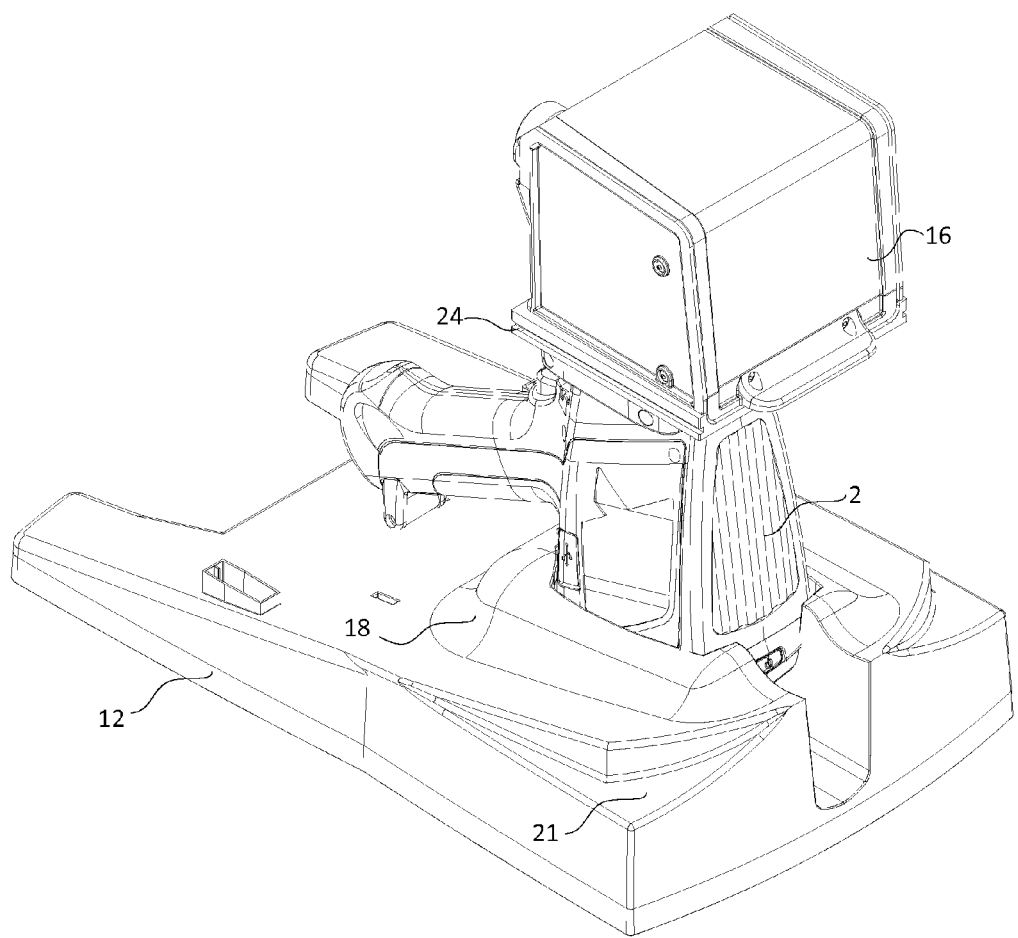
FIG. 1B is a perspective view of the test stand and the XRF analyzer in its vertical position according to the present disclosure.

Referring to FIGS. 1A and 1B, a test stand 10 primarily comprised of a test chamber 16, a base 12 and a stanchion 14 engages a handheld XRF analyzer (herein referred to as an analyzer 2). Test chamber 16 allows for critical positioning of samples under consideration while allowing both horizontal and vertical positioning of analyzer 2 and test chamber 16. The multiple analyzer orientations facilitate viewing and access to the sample and analyzer 2's LCD graphical user interface.

Figure 2A:
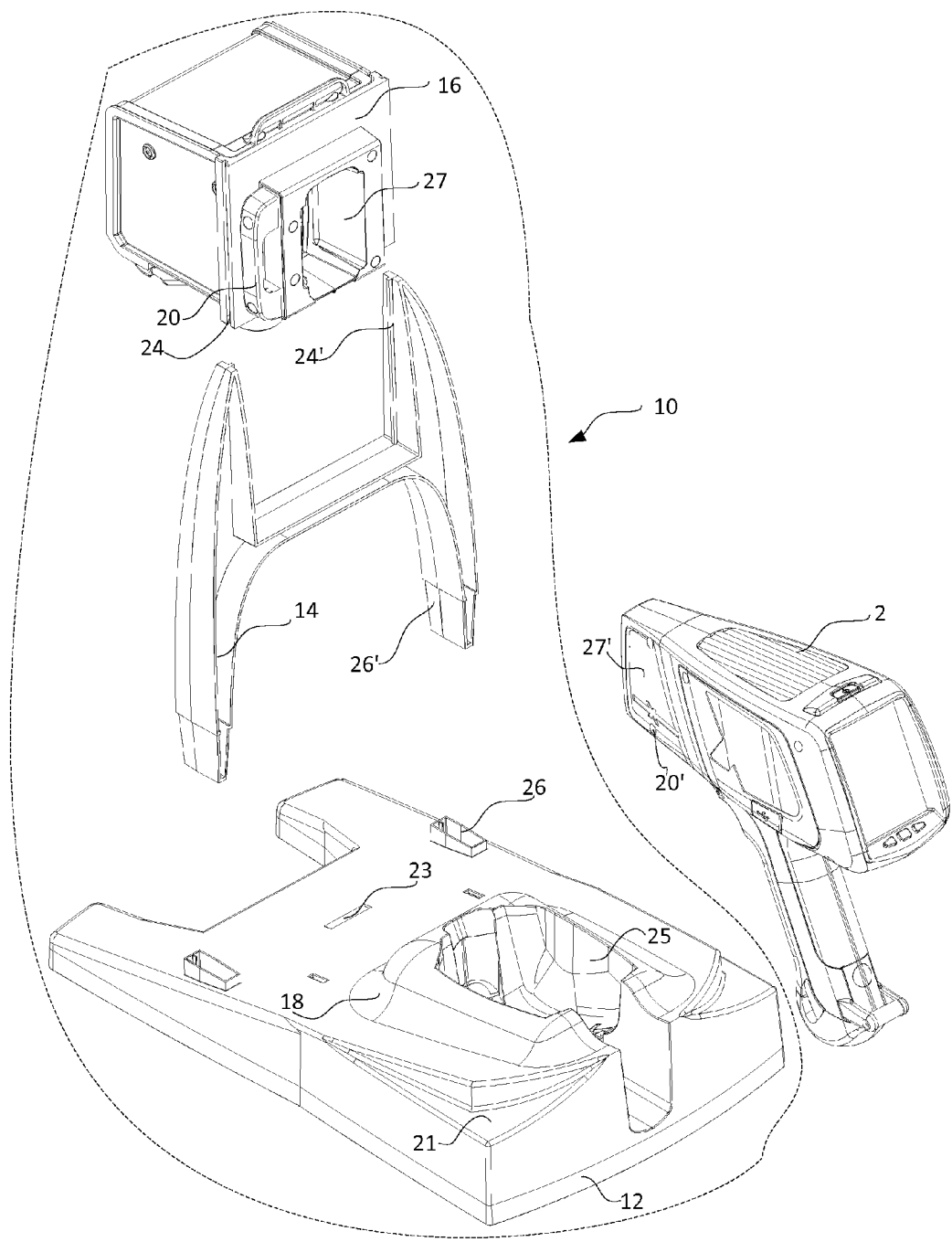
FIG. 2A is a perspective view of the test stand and of an XRF analyzer in its horizontal position, with more elaborated view of the stanchion.

Particularly, FIG. 1A shows analyzer 2 mounted in the horizontal orientation with (assembled) test chamber 16. As shown in FIG. 2A, analyzer 2 is held firmly in position via a release handle 20 which has locking pins that engage locking pin receptacles 20' in a snout 27 ' of analyzer 2. In this configuration, test chamber 16 is held in place, preferably, via an interface plate 24 in the aluminum part of chamber 16 with a corresponding interface plate tongue 24' in a stanchion 14. Both stanchion 14 and analyzer 2 are held in place in base 12 via corresponding features, a cavity 25 and a handle cradle 23, in base 12.

It should be appreciated that there can be many alternatives to attach test chamber 16 is attached to stanchion 14, and all such alternatives should be construed within the scope of the present disclosure.

Alternatively in FIG. 1B, analyzer 2 is mounted directly in base 12 in the vertical orientation by engaging a stability collar 18 and a cavity 25 within base 12. These features hold analyzer 2 and base 12 as an assembly in a stable and secure manner. As shown in FIG. 2A, analyzer 2 is fastened to test chamber 16 via release handle 20 and locking pin receptacles 20' within a snout 27 receiver.

Referring to FIG. 2A, the major components of test stand 10 and XRF analyzer 2 are shown with a more elaborated "pulled-out" view. Interface plate 24 shields the user from X-rays during operation and provides the structural rigidity for test chamber 16. Test chamber 16 interfaces with analyzer 2 while being supported via stanchion 14 that is inserted into a stanchion receiver 26 and being held in position by release handle 20. Stanchion 14 is shown separately which details both interface plate tongue 24' and stanchion leads 26'. FIG. 2A also shows base 12 separately with detailed features as embodiments. The details shown include stability collar 18 which holds analyzer 2 when in both the vertical and horizontal positions, handle cradle 23 which engages features on the handle of analyzer 2, and cavity 25 in which analyzer 2 is cradled during vertical operation. Base 12 also optionally contains additional stability wings 21, which add robust stability to the assembly when test chamber 16 and analyzer 2 are assembled.

Figure 2B:
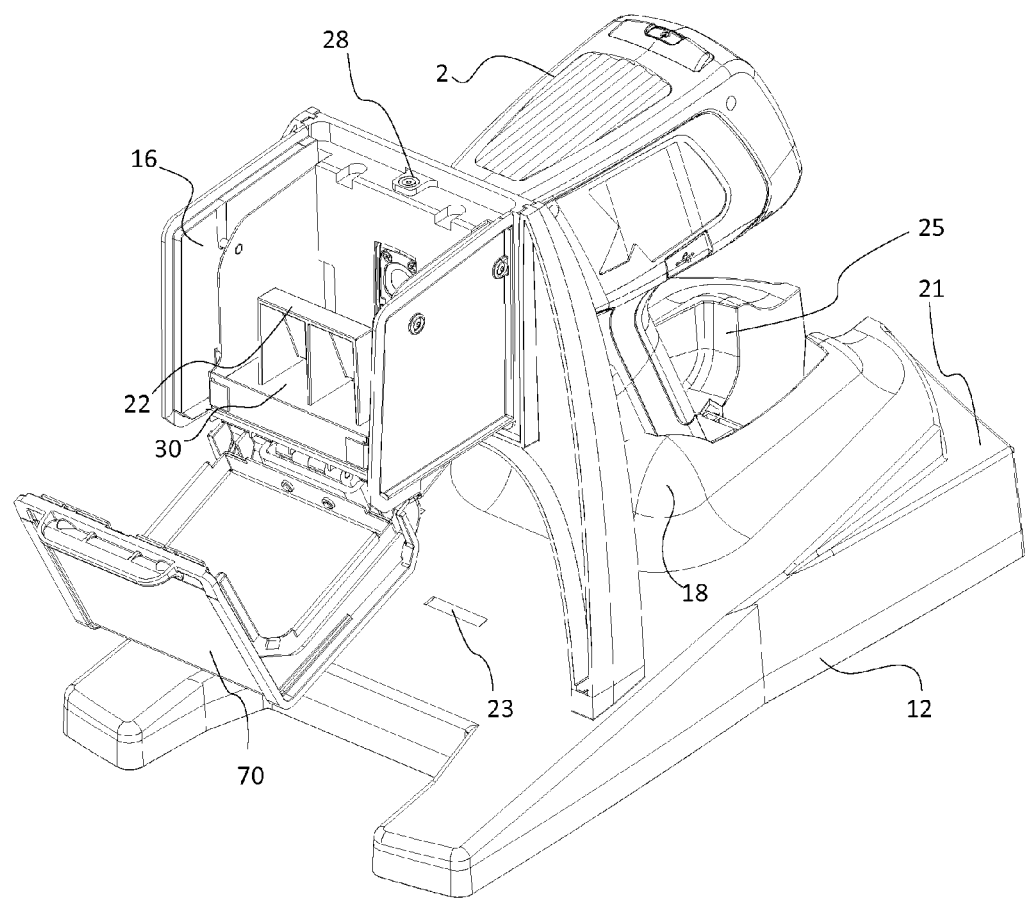
FIG. 2B is a perspective view of the test stand and the XRF analyzer in its horizontal position, showing a more elaborated view of a sample holder inside a test chamber.

Referring to FIG. 2B, the test stand is in the horizontal position with a test chamber door 70 of test chamber 16 open and its cavity ready to accept a sample. Shown is a soil sample retainer 22 mounted to a test platform 30. It is important to note that in the horizontal configuration, test platform 30 can be adjusted in height to facilitate proper placement and orientation in a vertical position. Soil sample retainer 22 can be adjusted fore and aft and aids in positioning the sample close to the detector window to optimize analysis. In addition, FIG. 2B shows a magnet 28 that secures test chamber door 70 in the closed position via a magnet stripe plate on test chamber door 70, although other means to secure the test stand door in the closed position may be used, and should be appreciated to fall under the scope of the present disclosure.

Figure 3A:
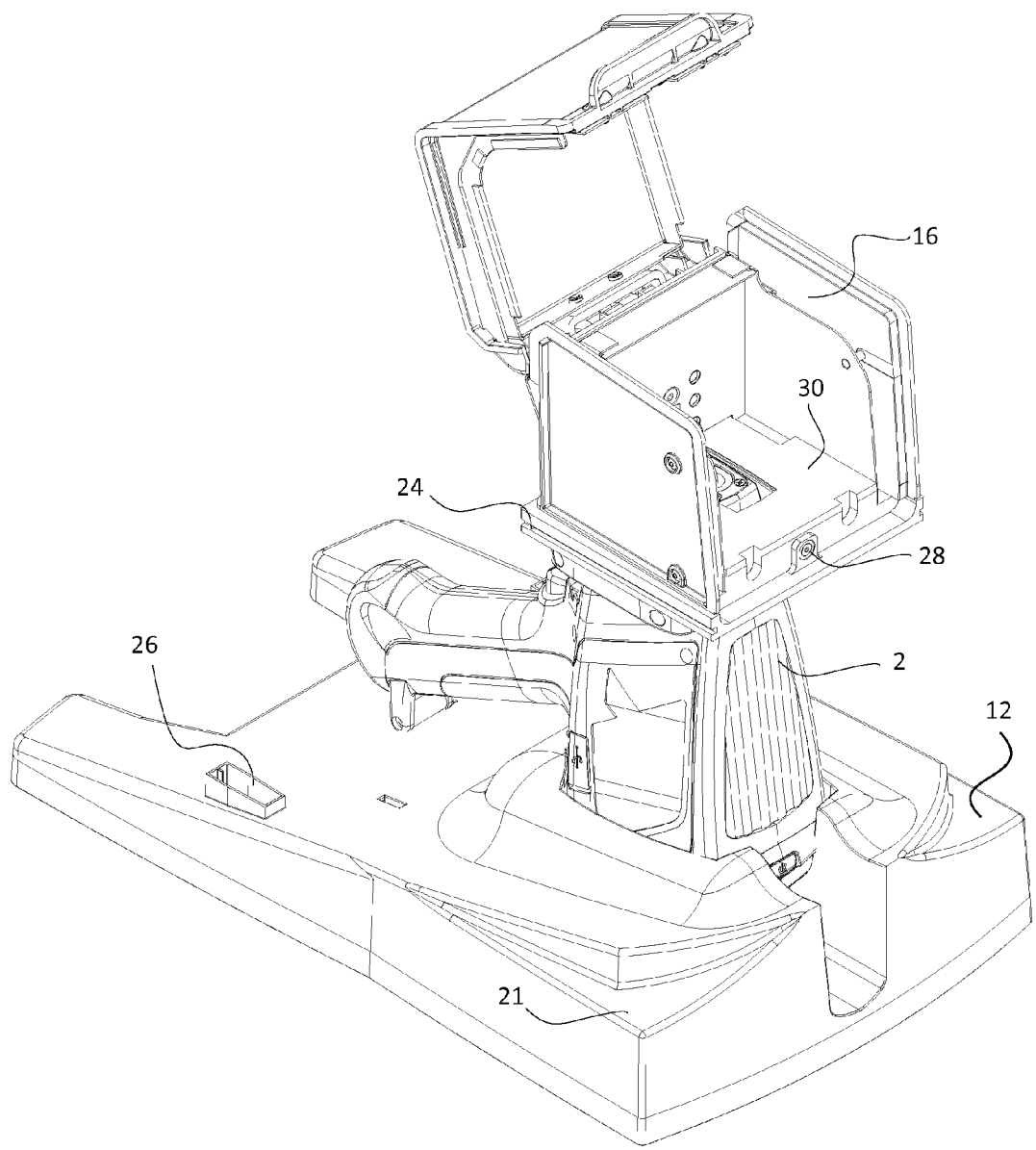
FIG. 3A is a perspective view of the test stand and the XRF analyzer in its vertical position, showing the loading view of the test chamber.

Referring to FIG. 3A, analyzer 2 is in the vertical position with the door of test chamber 16 open. In this orientation, test platform 30 is adjusted to its fully retracted position. Samples under test are placed directly on the test window of analyzer 2.

Figure 3B:
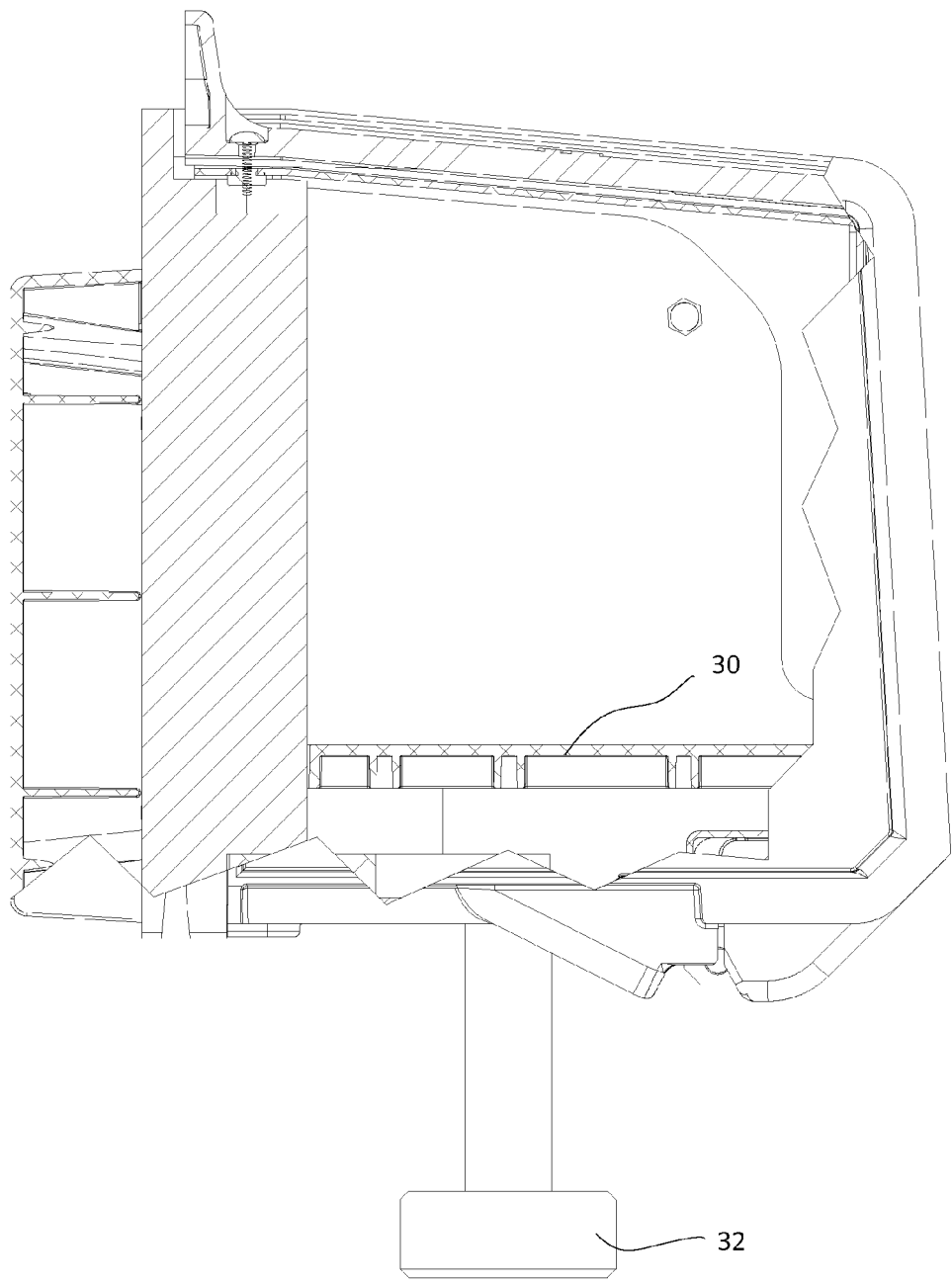
FIG. 3B is a cross-sectional view of the test chamber, showing the adjustment of a sample platform.

Referring to FIG. 3B, a cut-away view of test chamber 16 shows how test platform 30 can be raised and lowered with a test platform adjustment knob 32. The threaded fastener enables vertical adjustment of a sample under testing to the exact position as desired by the user.

Figure 4:
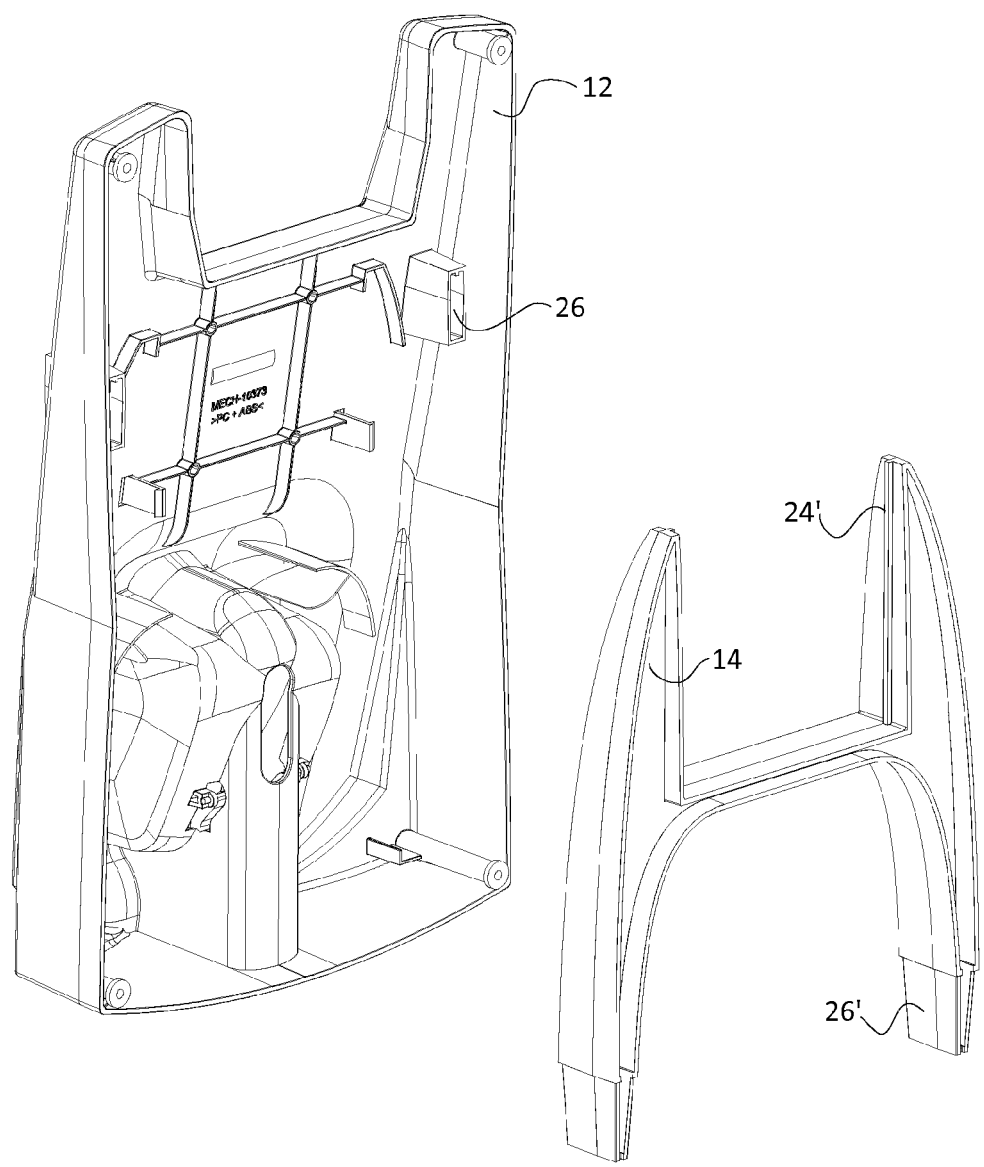
FIG. 4 is a perspective view of the bottom of the test stand, showing storage of a stanchion underneath the base of the stand.

Referring to FIG. 4, preferably stanchion 14 can be attached and stored under base 12 for easy carrying and saving storage space. The bottom of base 12 is therefore preferably molded with snap-in features which engage interface plate tongue 24'. Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of probes such as, but not limited to, Ultrasonic (UT) single element, multi-element, and array probes.

What is claimed is:

1. A supporting stand configured for supporting a handheld X-ray fluorescence (XRF) analyzer, the analyzer having a housing including more than one housing parts, each with a predetermined external geometric configuration, a viewing screen, and an analyzer opening with an analyzer window through which the X-ray is made to pass through, and wherein the window is coupled with a test chamber encasing test material being radiated by the X-ray during the operation of the analyzer, the stand comprising, a stand base configured to have a bottom sitting on top of a substantially horizontal planar test platform, and, a side opposite to the bottom and shaped with receptors configured to match the external geometric configuration of the more than one housing parts, and to hold the analyzer at more than one testing positions, and wherein one of the more than one housing parts is a first housing part having a first external shape and one of the receptors is a first receptor which is correspondingly shaped to mate with the first external shape, thereby holding the analyzer in an optional horizontal testing position, wherein the chamber is attached to the analyzer in a way such that the analyzer window and the chamber opening are coupled to allow the X-ray pass through substantially horizontally, and, wherein one of the more than one housing parts is a second housing part having a second external shape, and one of the receptors is a second receptor which is opposite to the analyzer opening and wherein the second receptor is correspondingly shaped to mate with the second external shape, thereby holding the analyzer in an optional vertical testing position, and the test chamber is removably attached to the analyzer in a way such that the test chamber is sitting on top of the analyzer opening and the analyzer window and the chamber opening are coupled to allow the X-ray pass through.

2. The stand of claim 1, wherein the chamber further comprising a chamber X-ray opening through which the X-ray is passed, a chamber cover with a chamber handle for opening and closing the chamber for the purpose of loading the test material, wherein the test chamber is made of material that can significant block the X-rays from being transmitted out of the chamber.

3. The stand of claim 1 further comprising a stanchion that works with the base and configured to support the analyzer and the chamber for at least one of the more than one testing positions.

4. The supporting stand of claim 1, wherein the first receptor and the first housing part are matched with a snap fit configuration contributing to maintain the analyzer in the horizontal testing position.

5. The supporting stand of claim 4, during the operation in the horizontal testing position, wherein the test chamber is affixed to the stanchion in a removable manner, and,
wherein the stanchion is in an erected position firmly yet removably standing on the base, contributing to maintain the analyzer in the horizontal testing position.

6. The supporting stand of claim 4, wherein the chamber and the stanchion are affixed via mating slot and ribs.

7. The supporting stand of claim 4, wherein the chamber and the analyzer are attached via one or more pairs of mating locking pins and pin-holes, wherein the locking pins are detached from the pin-holes via a lock handle, and attached via compression spring means.

8. The supporting stand of claim 4, wherein the chamber further comprising a loose test material container and container holding piece holding the test material in an erected manner, forming the test material facing the X-rays emitted by the analyzer, wherein the container holding piece is attached to the test chamber in a removable manner.

9. The supporting stand of claim 4, when the stanchion is not used, wherein the stanchion and the base are corresponding configured to allow the stanchion to be stored onto the base in a snap fit attachment.

10. The supporting stand of claim 1, wherein the first housing part is an analyzer handle.

11. The supporting stand of claim 1, wherein the second receptor and the second housing part with predetermined external geometric feature are matched with a snap fit configuration contributing to maintain the analyzer in the vertical testing position.

12. The supporting stand of claim 11, during the operation in the vertical testing position, wherein the test chamber is removably attached to the analyzer in a way such that the test chamber is sitting on top of the analyzer opening and the analyzer window and the chamber opening are coupled to allow the X-ray pass through.

13. The supporting stand of claim 12, wherein the chamber and the analyzer are attached via one or more pairs of mating locking pins and pin-holes, wherein the locking pins are detached from the pin-holes via a lock handle, and attached via compression spring means.

14. The supporting stand of claim 11, wherein the test chamber further comprising a test material loading platform for holding the test material, the loading platform is configured to be adjustable up and down by an adjusting means so that the test material is properly positioned to be radiated by the X-ray.

15. The supporting stand of claim 14, wherein the adjusting means is enabled by a screw bolt.

* * * * *